(12) United States Patent
Jarosz et al.

(10) Patent No.: US 11,053,537 B2
(45) Date of Patent: Jul. 6, 2021

(54) REVERSE COMPLEMENT ADAPTERS FOR THE MITIGATION OF UMI HOPPING

(71) Applicant: Integrated DNA Technologies, Inc., Coralville, IA (US)

(72) Inventors: Mirna Jarosz, Mountain View, CA (US); Madelyn Light, Redwood City, CA (US); Jiashi Wang, Belmont, CA (US); Kristina Giorda, San Mateo, CA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 0 days.

(21) Appl. No.: 15/989,784

(22) Filed: May 25, 2018

(65) Prior Publication Data

US 2018/0340216 A1 Nov. 29, 2018

Related U.S. Application Data

(60) Provisional application No. 62/511,133, filed on May 25, 2017.

(51) Int. Cl.
*C12Q 1/6855* (2018.01)
*C12Q 1/6806* (2018.01)
*C12N 15/10* (2006.01)
*C12Q 1/6848* (2018.01)
*C12Q 1/686* (2018.01)

(52) U.S. Cl.
CPC ....... *C12Q 1/6855* (2013.01); *C12N 15/1065* (2013.01); *C12Q 1/686* (2013.01); *C12Q 1/6806* (2013.01); *C12Q 1/6848* (2013.01)

(58) Field of Classification Search
CPC .............. C12N 15/1065; C12Q 1/6806; C12Q 1/6848; C12Q 1/6855; C12Q 1/686; C12Q 2525/191
USPC ............. 435/6.1, 6.12, 91.1, 91.31; 536/23.1
See application file for complete search history.

(56) References Cited

FOREIGN PATENT DOCUMENTS

CN 105401222 A * 3/2016

* cited by examiner

*Primary Examiner* — Jane J Zara
(74) *Attorney, Agent, or Firm* — John A. Petravich; David J. Youngkin

(57) ABSTRACT

The invention pertains to construction of next-generation DNA sequencing (NGS) libraries for whole genome sequencing, targeted resequencing, sequencing-based screening assays, metagenomics, or any other application requiring sample preparation for NGS.

4 Claims, 12 Drawing Sheets

Specification includes a Sequence Listing.

Final Library

18

REVERSE COMPLEMENT ADAPTERS FOR THE MITIGATION OF UMI HOPPING

CROSS-REFERENCE TO RELATED APPLICATIONS

This application claims benefit of priority under 35 U.S.C. 119 to U.S. provisional patent application bearing Ser. No. 62/511,133, filed May 25, 2017, and entitled "REVERSE COMPLEMENT ADAPTERS FOR THE MITIGATION OF UMI HOPPING," the contents of which are herein incorporated by reference in their entirety.

SEQUENCE LISTING

The instant application contains a Sequence Listing that has been submitted in ASCII format via EFS-Web and is hereby incorporated by reference in its entirety. The ASCII copy, created May 25, 2018, is named Sequence_Listing.txt, and is 2,816 bytes in size.

FIELD OF THE INVENTION

The invention pertains to construction of next-generation DNA sequencing (NGS) libraries for whole genome sequencing, whole exome sequencing, targeted resequencing, sequencing-based screening assays, metagenomics, or any other application requiring sample preparation for NGS.

BACKGROUND OF THE INVENTION

Next Generation Sequencing (NGS) has evolved into a very powerful tool in molecular biology, allowing for the rapid progress in fields such as genomic identification, genetic testing, drug discovery, and disease diagnosis. As this technology continues to advance, the volume of nucleic acids which can be sequenced at one time is increasing. This allows researchers to not only sequence larger samples, but to increase the number of reads per sample which allows for detection of small sequence variations within that sample.

As the volume and complexity of NGS processing increases, so does the rate of experimental error. While much of this error occurs in the sequencing and processing steps, they can also occur during the sample preparation steps. This is particularly true during the conversion of the sample into a readable NGS library by which adaptor sequences are attached to the ends of each fragment of a fragmented sample (library fragment) in a uniform fashion.

There are several types of errors that can occur during the execution of next generation sequencing (NGS), and it is important to be able to differentiate between true rare variants, such as rare alleles or mutations that exist in the patient, and errors that arise from sequencing and/or sample preparation. Particularly problematic are errors that are introduced introduced during library construction, prior to library amplification via PCR. Such can propogate during PCR, leading to multiple copies of sequences containing the error, making it difficult to to distinguish between the errors and true variants. The general strategy used to overcome this is consensus calling, whereby sequence reads that are PCR copies of a single, original fragment are grouped together and compared to similar groups of copies, derived from other original fragments, which overlap in sequence. If a variation is present in one group of clones and not the others, then is is most likely an error propogated by PCR whereas variations present in several groups are most likely true variants. In order perform this analysis, one must be able to differentiate between clones derived from one molecule and those derived from another.

The term "consensus sequence", as used herein, refers to a sequence obtained by comparing multiple sequences within a family of sequences. Sequence variations that are present in some, but not in the majority of sequences, in the family may be designated as errors and subsequently removed from the analysis. On the other hand, sequence variations that are present in the majority of sequences within a family may be designated as true variants that were present in the original genetic material being analyzed. The term "consensus calling", as used herein, refers to the process to determining if a genetic variation is a true variation or an error.

The term "variant calling", as used herein, refers to the process of determining if a sequence variation is a true variant derived from the original sample, and thus used in the analysis, or the result of a processing error and thrown out.

The term "family", as used herein, refers to a group of reads that are determined to be duplicates based on their having the same start stop sites and/or UMIs. In variant calling, large families with multiple clones are desireable since they can be used to build stronger consensus sequences than those with only a few clones to compare. For very small family sizes with one or two clones, a consensus can't be called, resulting in potentially important data being thrown out.

The term "deduplication", or "dedup", as used herein, refers to the removal of reads that are determined to be duplicates, from the analysis. Reads are determined to be duplicates if they share the same start stop sequences and/or UMI sequences. One purpose of deduplication is to create a consensus sequence whereby those duplicates which contain errors are removed from the analysis. Another purpose of deduplication is to estimate the complexity of the library. A library's "complexity", or "size", as used herein, refers to the number of individual sequence reads that represent unique, original fragments and that map to the sequence being analyzed.

The terms "start stop sites", "fragment ends" or "position-based", as used herein, refer to the sequences at the 5' and 3' ends of a sheared library fragment that become directly ligated to the sequencing adapters. Start stop sites can be used to determine if two similar sequences are derived from separate molecules or are cloned copies of the same original fragment. In order for different original fragments to have the same start stop sites, the shearing events that created them would have had to cleave at exactly the same sites, which has a low probability. Clones, on the other hand, should always have the same start stop sites. As such, any fragments that share the same start stop site (due to random shearing), are usually considered duplicates.

A "start stop collision", as defined herein, is the occurance of multiple unique fragments that contain the same start stop sites. Due to the rarity of start stop collisions, they are usully only observed when either performing ultra deep sequencing with a very high number of reads, such as when performing low variant detection, or when working with DNA samples that have a small size distribution, such as plasma DNA. As such, start stop sites may not be enough in those scenarios since one would run the risk erroneously removing unique fragments, mistaken as duplicates, during the deduplication step. In these cases, the incorporation of UMIs into the workflow can potentially rescue a lot of complexity.

The term "UMI", or "Unique Molecular Identifier", as used herein, refers to a tag, consisting of a sequence of degenerate bases, which is used to label original molecules in a sheared nucleic acid sample. In theory, due to the extremely large number of different UMI sequences that can be generated, no two original fragments should have the same UMI sequence. As such, UMIs can be used to determine if two, similar sequence reads are each derived from a different, original fragment or if they are simply duplicates, created during PCR amplification of the library, which were derived from the same original fragment.

UMIs are especially useful, when used in combination with start stop sites, for consensus calling of rare sequence variants. For example, if you have two fragments have the same start and stop site, but have a different UMI, what would overwise have been lumped together as two clones arising from the same original fragment can now be properly designated as unique molecules. As such, the use of UMIs combined with start stop often leads to a jump in the coverage number since unique fragments that would have been labeled as duplicates using start stop alone will be labelled as unique from each other due to them having different UMIs. It also helps improve the PPV by removing false positives. There is currently a lot of demand for UMIs, as there are some rare variants that can only be fould via consensus calling using UMIs.

There are some limitations to UMIs. One is a phenomenon we termed "UMI hopping", where one fragment will get multiple UMIs introduced during PCR. Our proposed model for this hopping is illustrated in FIG. 1A. In our model, there will be some unligated adapters left over after the ligation step which are carried over to the PCR amplification step. During PCR, both of the unligated adapters can act as primers. The unligated P5 reverse complement, that normally ligates on to the 5' end of the fragment (5' P5rc), can serve as a primer directly. The P7 adapter, which normally ligates on to the 3' end of the adapter (3' P7) can be copied by the P7 PCR primer, resulting in an extension product (5' P7) that can then act as a primer. The 5' P7 is predicted to be more problematic than the 5' P5rc because it is linearly amplified with each cycle of PCR, causing its concentration to increase while that of the 5' P5rc remains constant, and contains the UMI tag. As such, it is predicted that the 3' P7 is the main culprit in the resulting UMI hopping, creating duplications of fragments with different UMIs via annealing to those fragments and extending. The end result, shown in FIG. 1A, are copies derived from the same starting molecule, but with different UMI tags.

An example of UMI hopping is shown in FIG. 1B, where reads containing the same start stop sites (circled) have different UMI tags (speckled, striped and checkered). The fact that these reads represent a minor, 0.5 percent allele, meaning the the probability of start stop collision is very low, indicates that the multiple UMI tags resulted from UMI hopping.

"PPV", or Positive Predictive Value, is the probability that a sequence called as unique is actually unique. PPV=true positive/(true positive+false positive). "Sensitivity" is the probability that a sequence that is unique will be called as unique. Sensitivity=true positive/(true positive+false negative).

Provided herein are high throughput methods for NGS library construction based on novel adapter structures and sequences that can minimize the occurance of UMI hopping and accurately convert DNA samples into sequencing libraries in under a day. These and other advantages of the invention, as well as additional inventive features, will be apparent from the description of the invention provided herein.

SUMMARY OF THE INVENTION

The invention pertains to construction of next-generation DNA sequencing (NGS) libraries for whole genome sequencing, targeted resequencing, sequencing-based screening assays, metagenomics, or any other application requiring sample preparation for NGS. The proposed method involves the use of novel P5 and P7 adapters that contain a single UMI on the adapter that ligates on to the 5' end of the fragment (5' adapter), which, as we demonstrate here, leads to a dramatic decrease the occurance of UMI hopping when compared to P5 and P7 adapters that contain a single UMI on the adapter that ligates on to the 3' end of the fragment (3' adapter). Although initial work has focused on attachment of P5 and P7 adaptors for Illumina sequencing, this method could be used on alternate platforms which also require the attachment of one or more synthetic sequences (Ion torrent for example).

In one embodiment, adapters with sequences that are the reverse complement of the standard P5 and P7 adapters are used. This way, the UMI can remain on the P7 adapter so there is no need to change the standard protocol. The standard P7 is a 3' adapter. By using the reverse complement of the P7, it becomes a 5' adapter. The resulting library end product is the same as when standard P5 and P7 adapters are used.

In another embodiment, standard P5 and P7 adapters are used that have the UMI on the P5 adapter. As such, the 5' adapter is the UMI adapter.

In another embodiment, standard P5 and P7 adapters are used that have a UMI on both the P5 and P7 adapters.

The invention can be used for any application involving DNA sequencing, but is especially valuable for cancer diagnostics where detection of rare variants in mixed populations of tumor and normal DNA is crucial. The invention can also be used to construct sequencing libraries from FFPE samples. The invention can also be used to construct sequencing libraries from ultra-low inputs of DNA with or without PCR, which may aid in forensic or microbiological studies where limited quantities of DNA are available and/or PCR cannot be tolerated.

DESCRIPTION OF THE DRAWINGS

FIG. 4A illustrates the standard method of using the P5 and P7 adaptors. FIG. 4B illustrates the new strategy (RC) of attaching the reverse complements of the P5 and P7 adapters (P5rc and P7rc, respectively). In this strategy, we switch the P7 adapter itself, along with the UMI, from the 3' end to the 5' end. This is accomplished by using the reverse complements of the 5' P5 and 3' P7 adapters, 3' P5rc (17) and 5' P7rc (16), respectively. This essentially gives it the same structure, as shown in FIG. 4C, with the UMI still on the P7 adapter arm, and is compatible with standard Illumina PCR, sequencing primers. The final library product (18) is the same whether the standard or RC method is used. The RC method has the added benefit of a lower frequency of UMI hopping.

FIG. 5C shows the result with 10 ng of input. FIG. 5D shows the result with 25 ng of input.

EXAMPLE 1

This example serves to compare the frequency of UMI hopping when the UMI is located on the 3' adapter versus when it is located on the 5' adapter. Here, a library was prepared by ligating on 5' and 3' adapters that both contain a UMI, resulting in a library where each fragment has a UMI on both ends.

Extracted intact genomic DNA from cell line NA12878 (Coreill) was sheared to an average size of 300 bp using ultrasonic fragmentation (Covaris S220). Using a Kapa Hyper Prep kit, fragmented DNA was subjected to combined end-repair and A-tailing, followed by ligation on the 3' and 5' ends of the fragments with a 3' first ligation adapter and a 5' second ligation adapter.

The 3' first adapter (SEQ ID NO:1) contained: a first 8-base sample barcode, a first 6-base UMI and a P7 adaptor sequence with associated sites for read2 and index sequencing primers. The 5' second adapter (SEQ ID NO:2) contained: a second 8-base sample barcode with a sequence complementary to the first sample barcode, a second 6-base UMI and a P5 adaptor sequence with associated sites for read1 and index sequencing primers.

Following ligation, the library was subjected to a PCR-amplification using NEB's Q5 polymerase, with primers that contain sequences that are complimentary to the P5 and P7 adapters (SEQ ID NOs:7 and 8, respectively) under the following conditions:

98° C. for 45 seconds
12 cycles of: 98° C. 15 s, 60° C. for 30 seconds, 72° C. for 30 seconds
72° C. for 1 minute
4° C. hold The resulting product was sequenced on a MiSeq® sequencer (Illumina) using 2×150 paired-end reads and following the manufacturer's protocol.

Figure 1A:
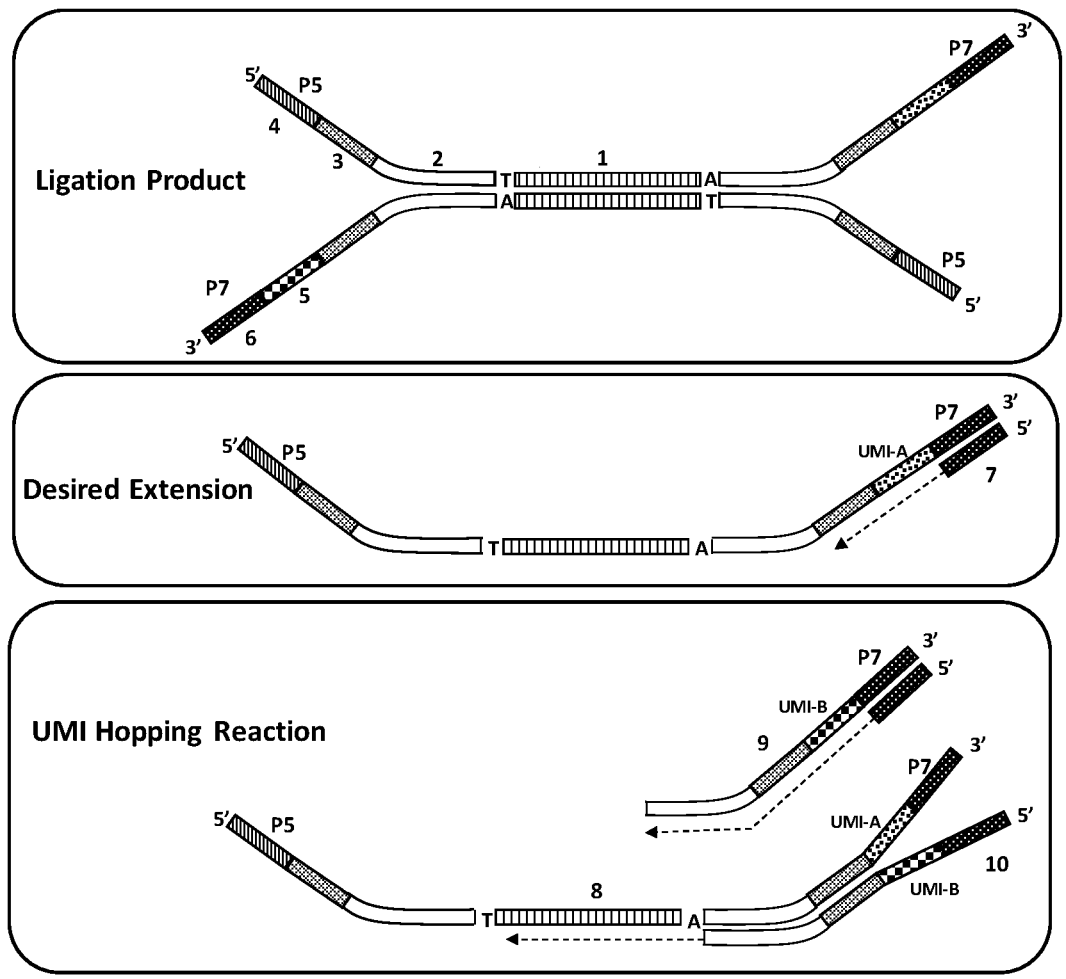
FIG. 1A illustrates our proposed mechanism for UMI hopping. The top panel shows the product after the ligation step, which contains the sample fragment (1), the double stranded stem region (2), dual matched sample barcodes on both the P5 and P7 arms (3), the 5' P5 adapter sequence (4), the 3' P7 adapter sequence (6), and the degenerate UMI sequence which in located on the 3' P7 adapter arm (5). The middle panel shows the desired extension reaction during the amplification step, where the P7 amplification primer (7) anneals to the 3' P7 sequence and extends, creating a reverse compliment copy of the library fragment with the correct UMI, UMI A in this case. The bottom panel shows the proposed UMI hopping reaction. Here, there is an unligated 3' P7 adapter with a different UMI sequence (9), UMI B in this case. The P7 amplification primer can prime off of the 3' P7 sequence of the unligated adapter, just as it does with the the 3' P7 sequence of the library fragment. The resulting extension product (10) is capable of annealing to the library fragmet on the 3' P7 arm via the sample index and the constant stem sequence. The resulting extension product is a reverse compliment of the library fragment (8), but with the UMI B sequence instead of the UMI A sequence. This results in two sequence reads, representing copies derived from the same original molecule, which have different UMI sequences. As such, these clones will be incorrectly called as unique sequences. If this happens frequently with many different molecules, it can lead to an overestimation of library complexity.
Figure 1B:
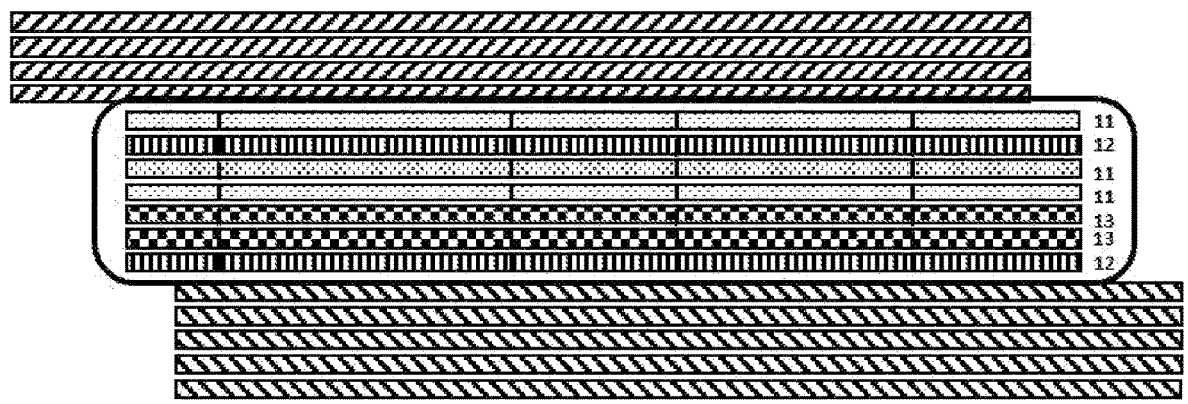
FIG. 1B shows an example of UMI hopping. Reads classified as originating from the same molecule, based on their having the same UMI sequences, are shown as having the same pattern (e.g. right-leaning stripes vs. left-leaning stripes). Aligned reads containing the same start stop sites, but with different UMI tags (circled), were falsely classified based on the different UMIs as arising from different original molecules (speckled, striped and checkered; corresponding to 11, 12 and 13 respectively). The fact that these reads represent a minor, 0.5 percent allele (SNPS represented by the verticle lines within each read), meaning the the probability of start stop collision happening three times is very low, indicates that the multiple UMI tags resulted from UMI hopping.
Figure 2A:
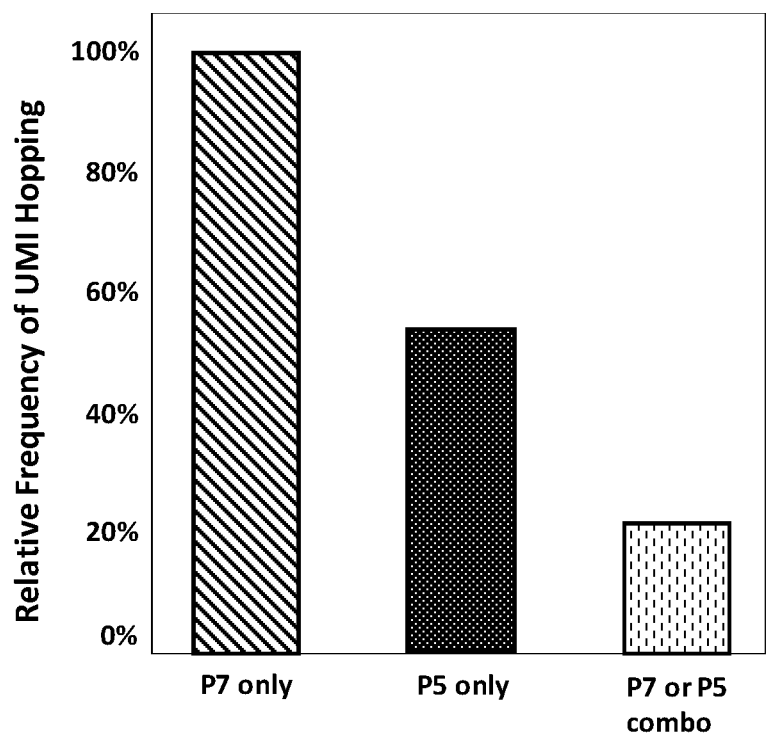
FIG. 2A demonstrates that UMI hopping is more frequent when the UMI is located on the 3' end vs the 5' end. Here libraries were prepared which contain UMIs on both the 3' P7 and 5' P5 adapters (SEQ ID NOs:1 and 2). The amount of hopping was estimated by dividing the number of unique reads using the UMI by that when using the start stop sites. The results show that when the UMI is located on the 5' P5 adapter, the hopping frequency is about 50 percent less than it is when the UMI is located in the 3' P7 adapter. Details of this experiment are provided in Example 1.

The sequencing information that was generated allowed us to compare the frequency of UMI hopping between the P7 (3') UMI and the P5 (5') UMI. Here, the UMI hopping frequency was determined by dividing the estimated library size, based on number of UMIs, by the estimated library size based on the number of different fragment ends. For the sake of comparison, the hopping frequency of the P5 (5') UMI is reported as a percentage of the hopping frequency of the P7 (3') UMI. As shown in FIG. 2A, the hopping frequency of the P5 (5') UMI is about 50 percent less that that of the P7 (3') UMI, supporting our hypothesis described above and illustrated in FIG. 1A.

Figure 2B:
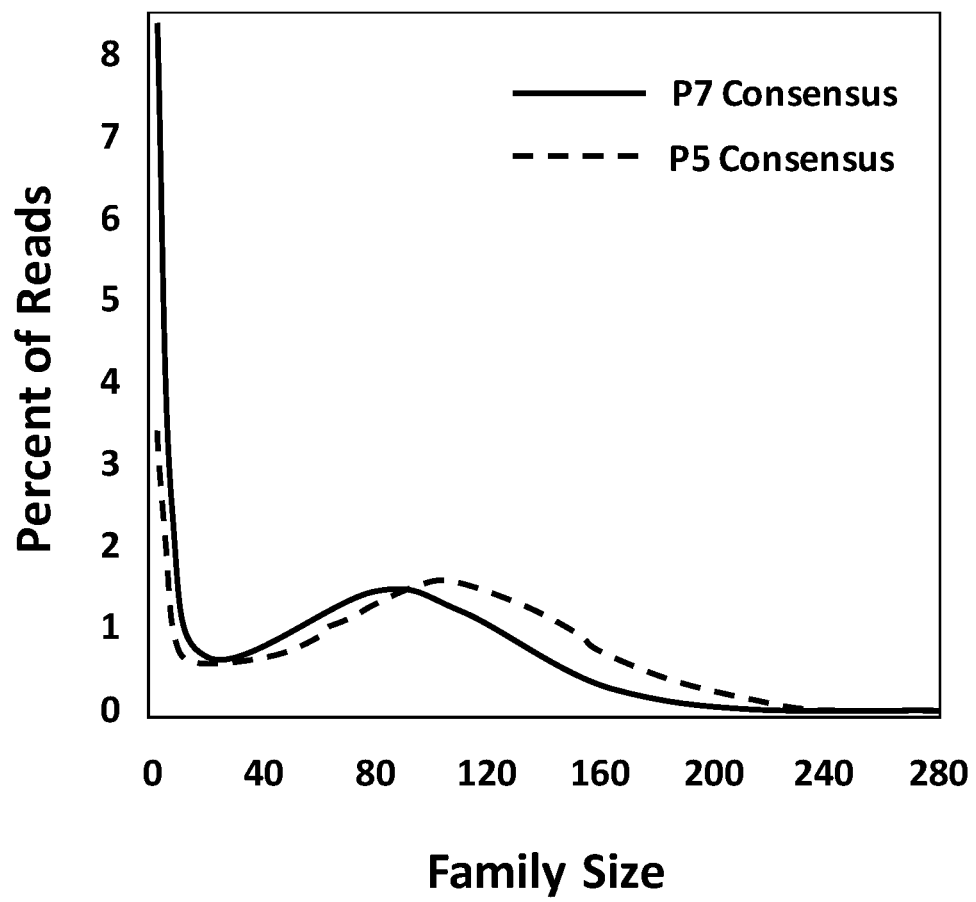
FIG. 2B is a histogram that shows how the difference in hopping frequency between the 5' P5 UMI and 3' P7 UMI affects the number of individual reads having both unique start-stop sites and UMIs (families), as well as the size of those families as determined by the number of copies of each unique sequence. Here, the number of very small families, with 1 to 2 copies, is higher when the consensus is determined using the 3' P7 UMI (solid line) when compared to that determined using the 5' P5 UMI (dashed line). On average, the family size is larger when the 5' P5 UMI is used (mean of around 110 copies) compared to when the 3' P7 UMI is used (mean of around 85 copies).

The sequencing information was also used to compare the number of individual reads, having both unique start stop sites and UMIs (families), that were generated using the P7 (3') UMI versus those generated using the P5 (5') UMI, as well as the number of clones within each family. On average, as is shown in FIG. 2B, the family sizes are larger when the P5 (5') UMIs are used in the analysis versus when the P7 (3') UMIs are used. Also, the number of very small families, containing only one or two clones, is lower for the P5 (5') UMI. This result supports our hypothesis where the higher frequency of UMI hopping for P7 (3') leads to a higher number of clones that were misidentified as unique sequences. In other words, clones derived from the same fragment ended up with different UMIs, leading to the misidentification. This was reduced when the P5 (5') UMI was used for the analysis.

Figure 3:
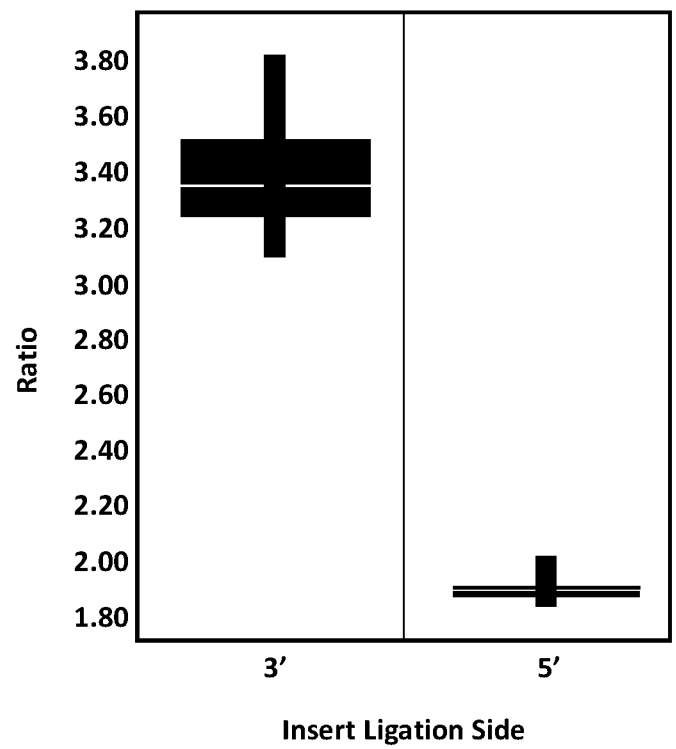
FIG. 3 shows a box plot representing the complexity of ten libraries, each containing UMIs on both their 3' P7 and 5' P5 adapters, when the 5' P5 UMIs or 3' P7 UMIs are used for the consensus calling. The complexity is estimated by determining the ratio of the estimated library complexity using UMI-based deduplication vs. the estimated library complexity using position-based deduplication. A higher ratio indicates a higher frequency of UMI hopping. As expected, the ration is higher, and more spread out, when the 3' P7 UMI is used for consensus calling when compared to when the 5' P5 UMI is used.
Figure 4A:
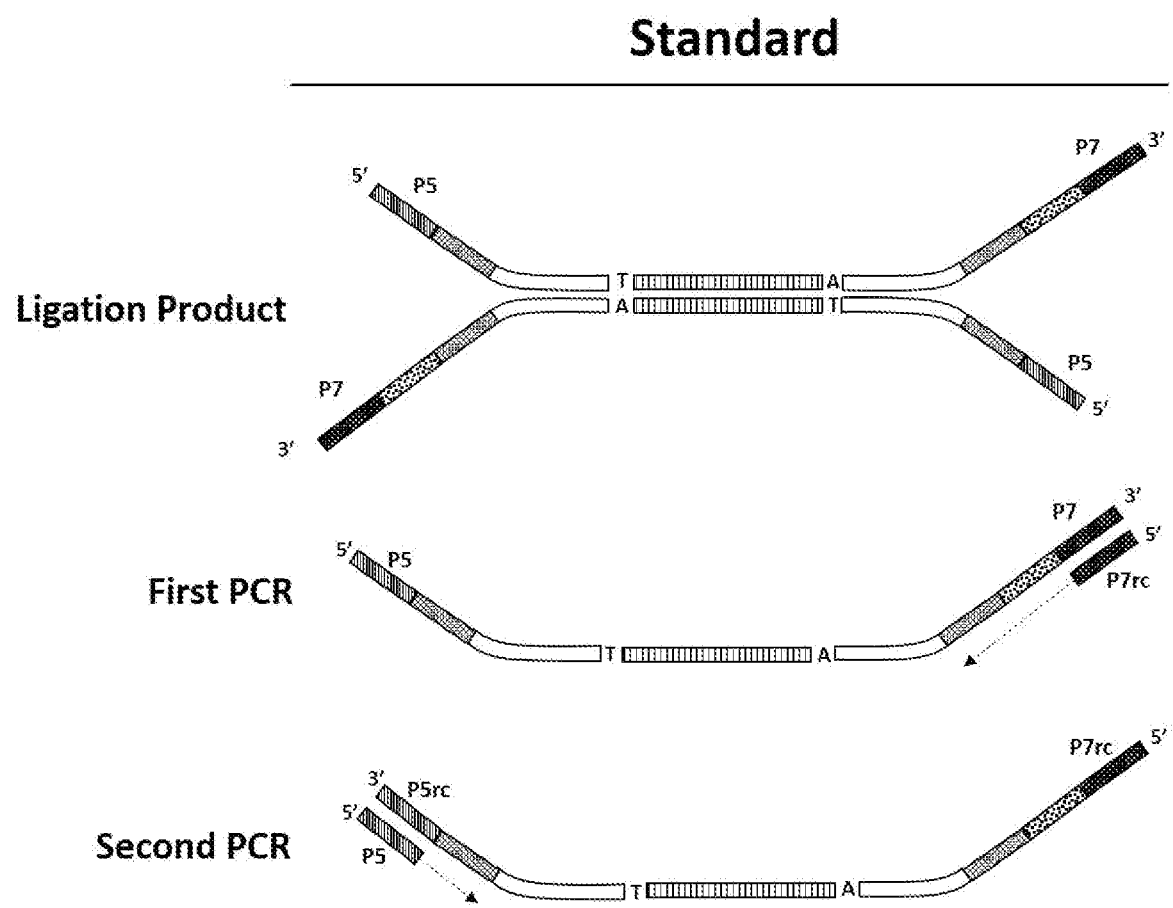
FIGS. 4A, 4B and 4C illustrate our strategy of placing the UMI on the 5' adapter, while keeping the work flow essentially the same as it is for the standard P5 and P7 adapters.
Figure 4B:
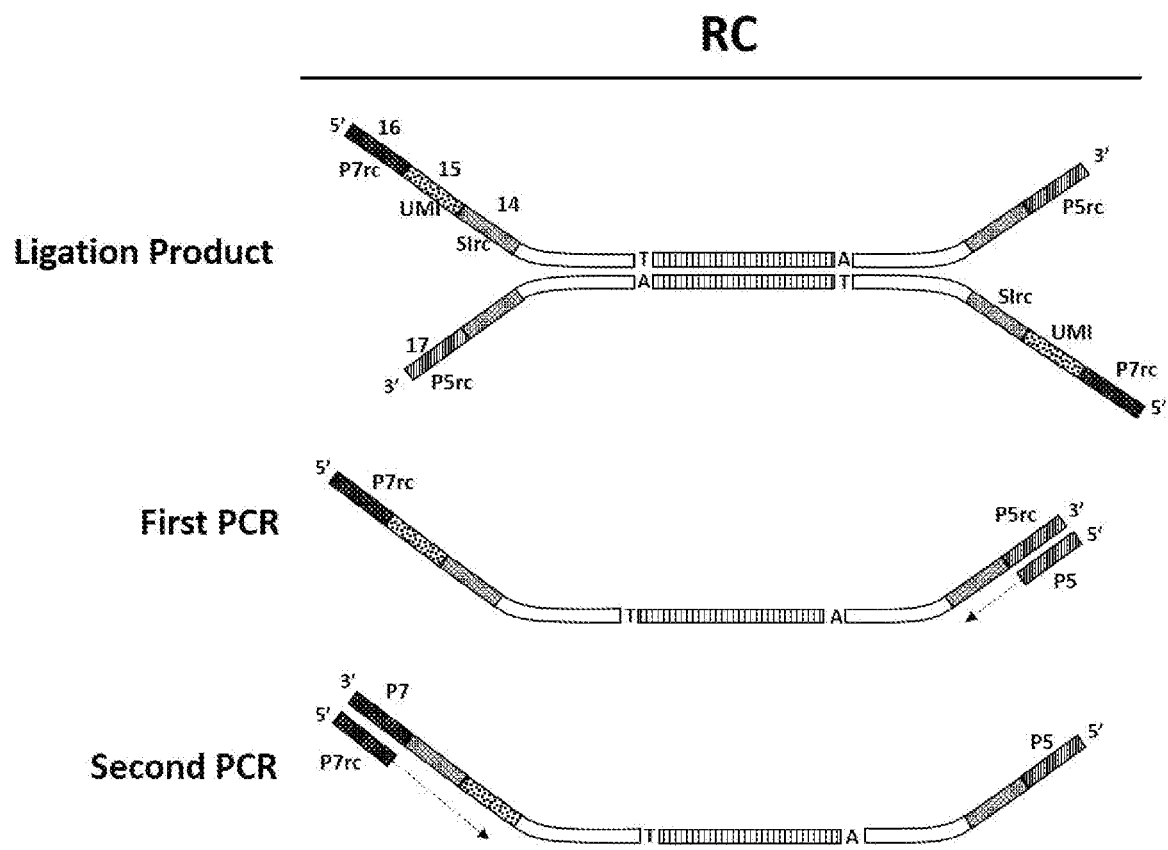
Figure 4C:

The above experiment was expanded such that the UMI hopping frequency was determined for 10 different libraries. The result, as is summarized in FIG. 3, further demonstrates that the UMI hopping frequency is higher for the P7 (3') adapter than for the P5 (5') adapter.

EXAMPLE 2

This example serves as an assessment of the libraries created using the reverse compliment adapters by comparing them with those created using the standard adapters with respect to yield, complexity and family sizes.

Figure 5A:
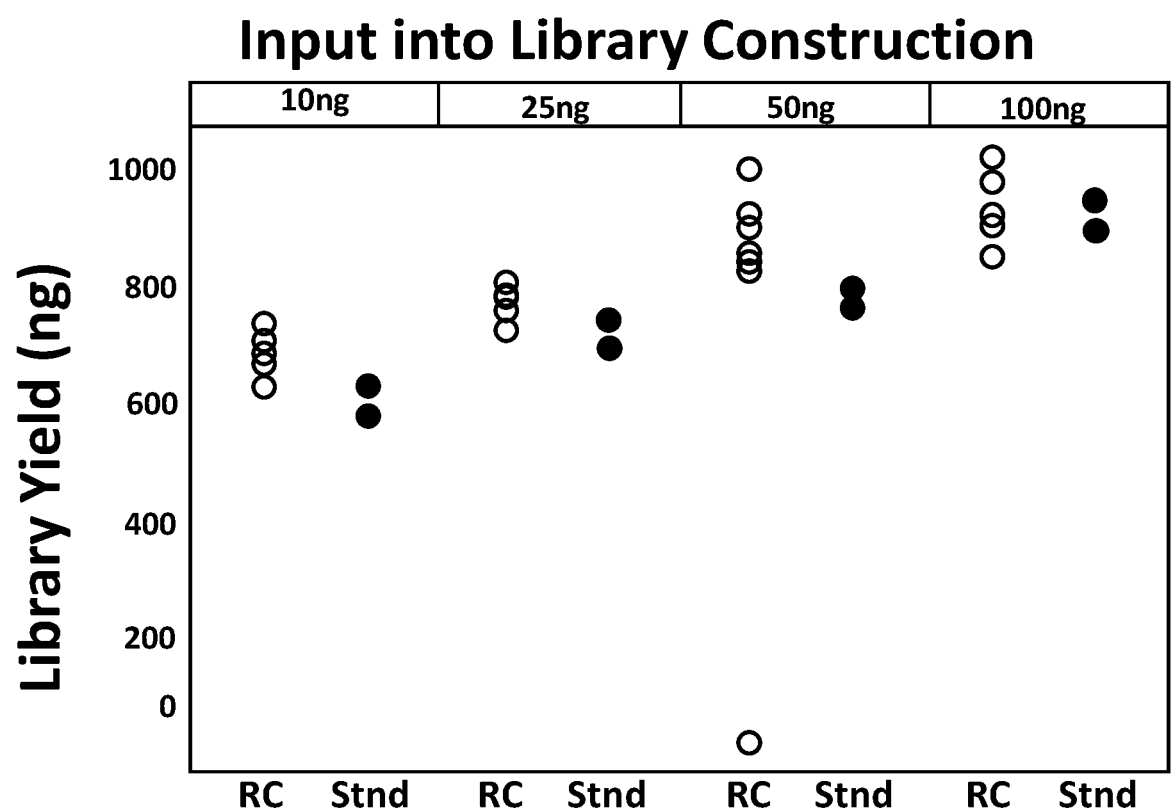
FIG. 5A compares the standard Illumina library (closed circles) with the RC library (open circles) with respect to library yield as a function of genomic DNA input. In this experiment, we did an input titration by which 10, 25, 50 and 100 ng of starting genomic material was added to the system and the the library yield was determined in ng DNA. As can be seen in the figure, the yields are similar between the standard and RC libraries, showing the same positive correlation between the amount of genomic input and library yield.

Libraries were made, using either the standard (SEQ ID NOs:1 and 3) or RC adapters (SEQ ID NOs:5 and 6), with inputs of 10, 25, 50 and 100 ng of sheared genomic DNA. The libraries were enriched via a custom IDT lockdown panel, and sequenced on the MiSeq. The yield for each library, as measured by total ng of library DNA recovered, is similar for the standard and RC libraries, both showing the same positive correlation between the amount of genetic input and the amount of library output as is shown in FIG. 5A.

Figure 5B:
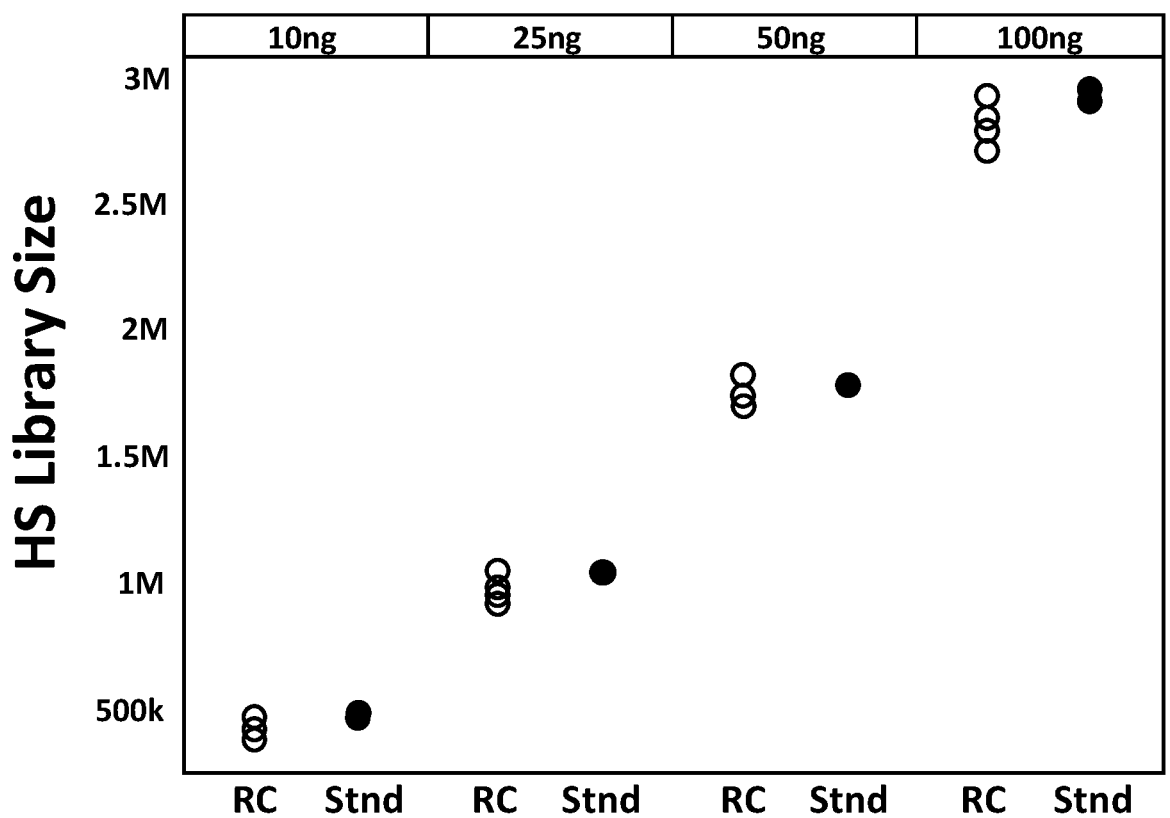
FIG. 5B shows that the complexities of the standard (closed circles) and RC (open circles) libraries, as determined by the number of unique sequences that map to the sequence being analyzed, are equivalent. They both have the same positive correlation between the amount of genomic input and library complexity.
Figure 5C:
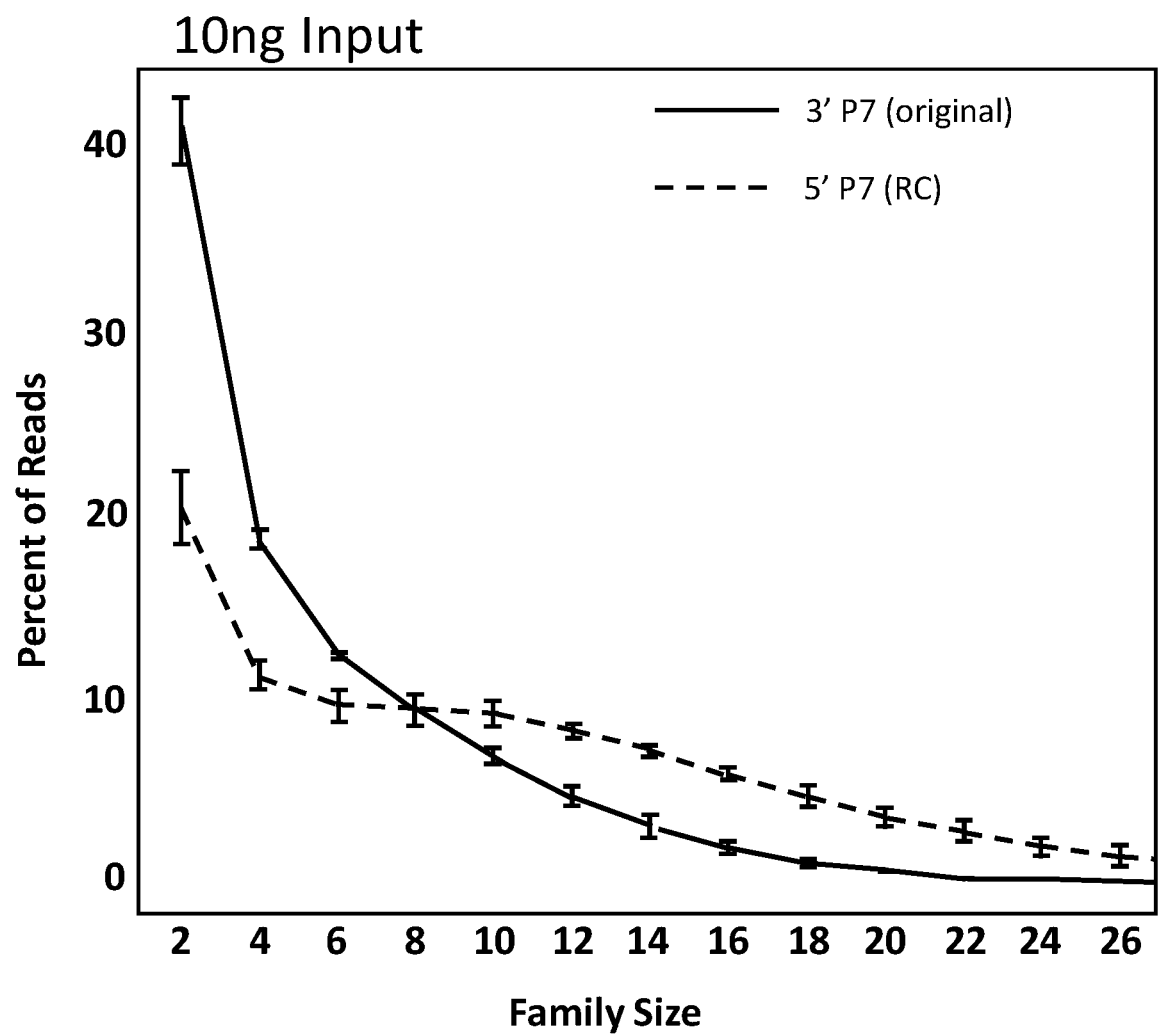
FIGS. 5C and 5D compare the family sizes between the standard (solid line) and RC (dashed line) libraries when the 3' P7 of the standard library or the 5' P7rc of the RC library are used for consensus calling using the method described in Example 1. The result of the comparison is similar to the one between the 5' P5 and 3' P7 adapters. Here the percent of very small are diminished when the RC UMI is used for consensus calling when compared to that when the standard UMI is used. Also, the average family size is larger for the RC UMI.
Figure 5D:
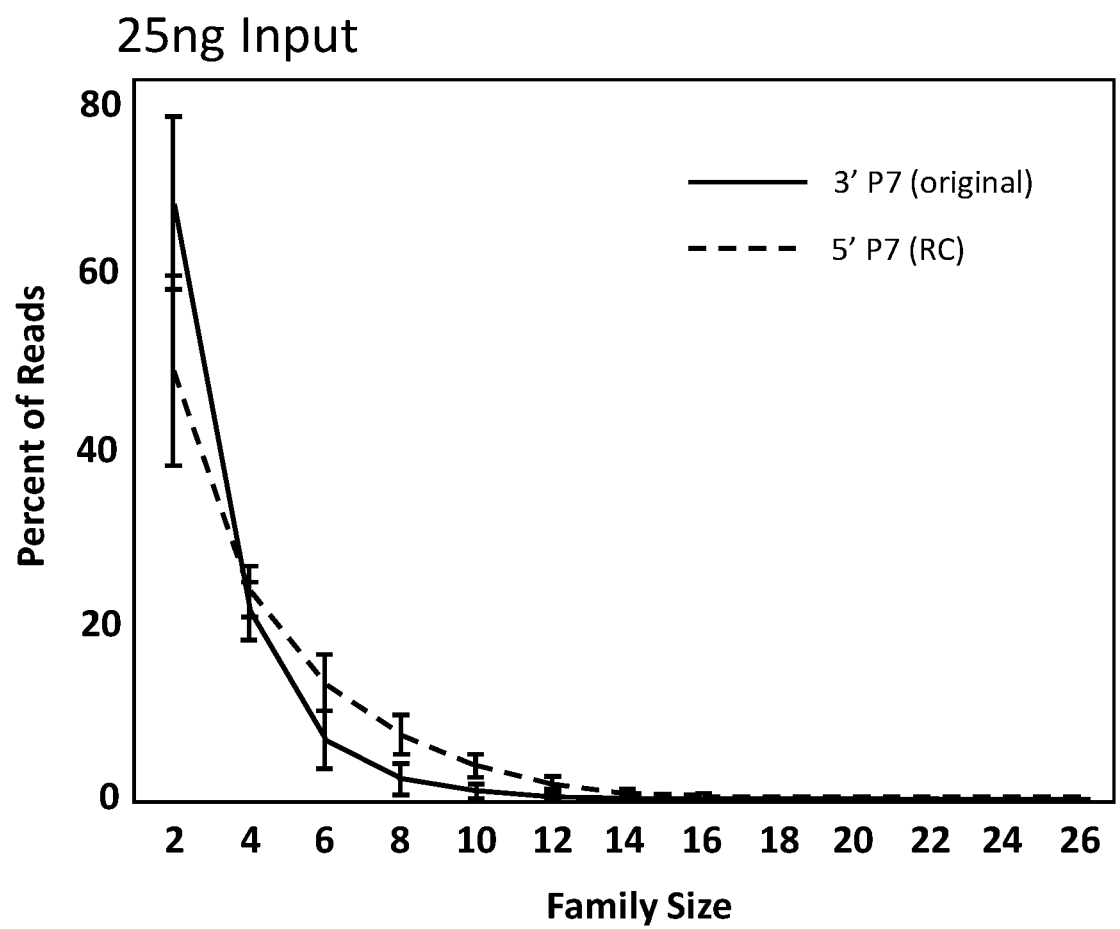

The library complexities, defined as the measure of the unique molecules that are mapping to the target region, was determined for standard and RC libraries. As is shown in FIG. 5B, the final library complexities of the standard and RC libraries are equivalent. This indicates that the RC adapters are just as functional as the standard ones, since an equivalent complexity indicates an equivalent rate of conversion from genomic sample to final library.

Finally, the family sizes were compared between the standard and RC libraries created using either the 10 or 25 ng input of sheared genomic DNA. Similar to that which was demonstrated with the P7 (3') and P5 (5') libraries in Example 1, the family sizes are, on average, larger when the RC UMIs are used in the analysis versus when the standard UMIs are used. Also, the number of very small families, containing only one or two clones, is lower for the RC library. All in all, this demonstrates that the RC adapters are just as effective as the P5 (5') adapters in diminishing the UMI hopping that leads to the misidentification of clones as sequences of different origins and the underestimation of family sizes.

EXAMPLE 3

This example serves to verify the mechanism of UMI hopping described above, and illustrated in FIG. 1A, by which the presence of unligated 3' adapter during the amplification step leads to UMI hopping when the UMI is located on that 3' adapter. Here, the amount of 3' and 5' library adapters, where the UMI is present on the 3' adapter, present during the PCR step is varied in order to determine if there is a positive correlation between the amount of the UMI-containing 3' adapter and the level of UMI hopping.

Extracted intact genomic DNA (10 ng) from cell line NA12878 (Coreill) was sheared to an average size of 300 bp using ultrasonic fragmentation (Covaris S220). Using a Kapa Hyper Prep kit, fragmented DNA was subjected to combined end-repair and A-tailing, followed by ligation on the 3' and 5' ends of the fragments with a 50/50 mixture of a 3' first ligation adapter and a 5' second ligation adapter, the concentration of the mixture being either 1, 4, or 16 uM.

The 3' first adapter contained: an 8-base sample barcode, a 6-base unique molecular identifier and a P7 adaptor sequence with associated sites for read2 and index sequencing primers (SEQ ID No. 1). The 5' second adapter contained: a second sample barcode with the complementary sequence of the first sample barcode and a P5 adaptor sequence with associated sites for read1 and index sequencing primers (SEQ ID No. 3).

Following ligation, the library was subjected to a PCR-amplification using NEB's Q5 polymerase, with primers that contain sequences that are complimentary to the P5 and P7 adapters (SEQ ID NOs:7 and 8, respectively) under the following conditions:

98° C. for 45 seconds 12 cycles of: 98° C. 15 s, 60° C. for 30 seconds, 72° C. for 30 seconds 72° C. for 1 minute 4° C. hold The resulting product was sequenced on a MiSeq® sequencer (Illumina) using 2×150 paired-end reads and following the manufacturer's protocol.

The sequencing data, shown in Table 1, shows that increasing amount of adapter present during PCR increases the frequency of UMI-hopping when the UMI is located on the P7 (3') adapter. Here, the UMI hopping frequency is determined by dividing the estimated library size, based on number of UMIs, by the estimated library size based on the number of different fragment ends. This supports the hypothesis that, during the PCR step, the P7 primer is hybridizing to, and extending off of, the leftover unligated P7 adapters, resulting in an extension product that can then act as a primer to introduce new UMI onto fragments.

TABLE 1

| P5/P7 Adapter Concentration (μM) | Estimated library Size Based on Number of Unique UMIs counted | Estimated library Size Based on Number of Unique Fragment Ends | Ratio of UMI to Ends-based on library Size Estimations |
|---|---|---|---|
| 16 | 7,061,841 | 899,135 | 7.85 |
|  | 6,438,537 | 743,237 | 8.66 |
| 4 | 3,213,921 | 940,741 | 3.42 |
|  | 2,306,965 | 833,767 | 2.77 |
| 1 | 813,075 | 478,467 | 1.7 |
|  | 2,075,368 | 1,199,806 | 1.73 |

EXAMPLE 4

This example serves to show that the UMI hopping is less pronounced when the UMI is located on the 5' adapter that it is when the UMI is located on the 3' adapter. In this case, the amount of 3' and 5' library adapters, where the UMI is now present on the 5' adapter, present during the PCR step is varied in order to compare the correlation between the amount of the UMI-containing 5' adapter and the level of UMI hopping with the amount of UMI hopping found in Example 1 where the UMI was on the 3' adapter.

Extracted intact genomic DNA (10 ng) from cell line NA12878 (Coreill) was sheared to an average size of 300 bp using ultrasonic fragmentation (Covaris S220). Using a Kapa Hyper Prep kit, fragmented DNA was subjected to combined end-repair and A-tailing, followed by ligation on the 3' and 5' ends of the fragments with a 50/50 mixture of a 3' first adapter and a 5' second ligation adapter, the concentration of the mixture being either 1, 4, or 16 uM.

The 3' first adapter contained: an 8-base sample barcode and a P7 adaptor sequence with associated sites for read2 and index sequencing primers (SEQ ID No. 4). The 5' second adapter contained: a second sample barcode with the complementary sequence of the first sample barcode, a 6-base unique molecular identifier and a P5 adaptor sequence with associated sites for read1 and index sequencing primers (SEQ ID No. 2).

Following ligation, the library was subjected to a PCR-amplification using NEB's Q5 polymerase, with primers that contain sequences that are complimentary to the P5 and P7 adapters (SEQ ID NOs:7 and 8, respectively) under the following conditions:

98° C. for 45 seconds
12 cycles of: 98° C. 15 s, 60° C. for 30 seconds, 72° C. for 30 seconds
72° C. for 1 minute
4° C. hold The resulting product was sequenced on a MiSeq® sequencer (Illumina) using 2×150 paired-end reads and following the manufacturer's protocol.

The sequencing data, shown in Table 2, shows that the ratio of the estimated library size based on number of UMIs to the estimated library size based on number of different fragment ends increases with an increase of adapter concentration when the UMI is present on the 5' adapter, but not as dramatically as when the UMI is present on the 3' adapter as shown in Table 1. This supports the model where UMI hopping is mitigated when the UMI is placed on the 5' adapter when compared to when the UMI is on the 3' adapter.

TABLE 2

| P5/P7 Adapter Concentration (μM) | Estimated library Size Based on Number of Unique UMIs counted | Estimated library Size Based on Number of Unique Fragment Ends | Ratio of UMI to Ends-based on library Size Estimations |
|---|---|---|---|
| 16 | 1,767,093 | 616,763 | 2.87 |
|  | 1,137,566 | 523,366 | 2.17 |
| 4 | 1,529,780 | 583,700 | 2.62 |
|  | 950,390 | 502,649 | 1.89 |
| 1 | 921,139 | 492,657 | 1.87 |
|  | 1,082,280 | 565,928 | 1.91 |

TABLE 3

| SEQ ID NOs: | | |
|---|---|---|
| P7 adapter with UMI | /5Phos/AGATCGGAAGAGCACACGTCTGAACTCCAG TCACgacacagtNNNNNNNNNNATCTCGTATGCCGTCTT CTGCTTG | SEQ ID NO: 1 |
| P5 adapter with UMI | AATGATACGGCGACCACCGAGATCTACACNNNNNN NNgacacagtACACTCTTTCCCTACACGACGCTCTTCC GAT*C | SEQ ID NO: 2 |
| P5 adapter without UMI | AATGATACGGCGACCACCGAGATCTACACgacacagtA CACTCTTTCCCTACACGACGCTCTTCCGAT*C | SEQ. ID NO: 3 |
| P7 adapter without UMI | /5Phos/AGATCGGAAGAGCACACGTCTGAACTCCAG TCACgacacagtATCTCGTATGCCGTCTTCTGCTTG | SEQ. ID NO: 4 |
| P7rc adapter | CAAGCAGAAGACGGCATACGAGATNNNNNNNNactgt gtcGTGACTGGAGTTCAGACGTGTGCTCTTCCGATC* T | SEQ. ID NO: 5 |
| P5rc adapter | /5Phos/GATCGGAAGAGCGTCGTGTAGGGAAAGAGT GTactgtgtcGTGTAGATCTCGGTGGTCGCCGTATCATT | SEQ. ID NO: 6 |
| P5 PCR primer | AATGATACGGCGACCACCGAGATCTACAC | SEQ. ID NO: 7 |
| P7 PCR primer | CAAGCAGAAGACGGCATACGAGAT | SEQ ID NO: 8 |

Six base degenerate sequence represented by N. Lower cases designate sample index sequence. Asterisk represents a phosphorothioate linkage.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of preparing a target nucleic acid fragment for sequencing, the method comprising:
   a. ligating a partially duplexed adapter to the ends of the target nucleic acid wherein the partially duplexed adapter has a top strand and a bottom strand;
      i. wherein the top strand comprises from the 5' to 3' direction a P7rc sequence, optionally a UMI sequence, optionally a sample index sequence and a sequence complementary to the bottom strand; and
      ii. wherein the bottom strand comprises from the 3' to 5' direction a P5rc sequence, optionally a second UMI sequence, optionally a sample index sequence, and a sequence complementary to the top strand.

2. The method of claim 1 wherein the top strand sample index sequence and the bottom strand sample index sequence are different.

3. The method of claim 1 wherein the top strand sample index sequence and the bottom strand sample index sequence are the same.

4. A method of preparing a target nucleic acid fragment for sequencing, the method comprising:
   a. ligating a partially duplexed adapter to the ends of the target nucleic acid wherein the partially duplexed adapter has a top strand and a bottom strand;
      i. wherein the top strand comprises SEQ ID NO: 5 and wherein the bottom strand comprises SEQ ID NO: 6.

* * * * *

SEQUENCE LISTING

```
<160> NUMBER OF SEQ ID NOS: 8

<210> SEQ ID NO 1
<211> LENGTH: 74
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5Phos
<220> FEATURE:
<221> NAME/KEY: misc_feature
<222> LOCATION: (43)..(50)
<223> OTHER INFORMATION: n is a, c, g or t

<400> SEQUENCE: 1
agatcggaag agcacacgtc tgaactccag tcacgacaca gtnnnnnnnn atctcgtatg     60
ccgtcttctg cttg                                                      74

<210> SEQ ID NO 2
<211> LENGTH: 77
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: n is a, c, g or t
<220> FEATURE:
<221> NAME/KEY: misc_feature
<222> LOCATION: (77)..(77)
<223> OTHER INFORMATION: Phosphorothioate linkage

<400> SEQUENCE: 2
aatgatacgg cgaccaccga gatctacacn nnnnnnngac acagtacact ctttccctac     60
acgacgctct tccgatc                                                   77

<210> SEQ ID NO 3
<211> LENGTH: 69
<212> TYPE: DNA
<213> ORGANISM: Artificial Sequence
<220> FEATURE:
```

<223> OTHER INFORMATION: synthetic nucleic acid
<220> FEATURE:
<221> NAME/KEY: misc_feature
<222> LOCATION: (69)..(69)
<223> OTHER INFORMATION: Phosphorothioate linkage

<400> SEQUENCE: 3
aatgatacgg cgaccaccga gatctacacg acacagtaca ctctttccct acacgacgct     60
cttccgatc                                                            69

<210> SEQ ID NO 4
<211> LENGTH: 66
<212> TYPE: DNA
<213> ORGANISM: Artificial Sequence
<220> FEATURE:
<223> OTHER INFORMATION: synthetic nucleic acid

<400> SEQUENCE: 4
agatcggaag agcacacgtc tgaactccag tcacgacaca gtatctcgta tgccgtcttc     60
tgcttg                                                               66

<210> SEQ ID NO 5
<211> LENGTH: 74
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: n is a, c, g or t
<220> FEATURE:
<221> NAME/KEY: misc_feature
<222> LOCATION: (74)..(74)
<223> OTHER INFORMATION: Phosphorothioate linkage

<400> SEQUENCE: 5
caagcagaag acggcatacg agatnnnnnn nnactgtgtc gtgactggag ttcagacgtg     60
tgctcttccg atct                                                      74

<210> SEQ ID NO 6
<211> LENGTH: 69
<212> TYPE: DNA
<213> ORGANISM: Artificial Sequence
<220> FEATURE:
<223> OTHER INFORMATION: synthetic nucleic acid

<400> SEQUENCE: 6
gatcggaaga gcgtcgtgta gggaaagagt gtactgtgtc gtgtagatct cggtggtcgc     60
cgtatcatt                                                            69

<210> SEQ ID NO 7
<211> LENGTH: 29
<212> TYPE: DNA
<213> ORGANISM: Artificial Sequence
<220> FEATURE:
<223> OTHER INFORMATION: synthetic nucleic acid

<400> SEQUENCE: 7
aatgatacgg cgaccaccga gatctacac                                      29

<210> SEQ ID NO 8
<211> LENGTH: 24
<212> TYPE: DNA
<213> ORGANISM: Artificial Sequence

```
<220> FEATURE:
<223> OTHER INFORMATION: synthetic nucleic acid

<400> SEQUENCE: 8
caagcagaag acggcatacg agat                                              24
```